United States Patent [19]
Cure

[11] 4,121,749
[45] Oct. 24, 1978

[54] METHOD OF MAKING THERMOCOUPLE

[75] Inventor: Omer P. Cure, Diepenbeek, Belgium

[73] Assignee: Electro-Nite Co., Philadelphia, Pa.

[21] Appl. No.: 805,362

[22] Filed: Jun. 10, 1977

Related U.S. Application Data

[62] Division of Ser. No. 672,100, Mar. 31, 1976, Pat. No. 4,056,407.

[51] Int. Cl.² .................. B23K 31/00; B01J 17/00
[52] U.S. Cl. .................. 228/173 A; 29/573; 136/233; 228/173 E; 228/178; 228/179
[58] Field of Search .............. 136/232, 233; 29/573; 228/173 A, 173 E, 178, 179

[56] References Cited

U.S. PATENT DOCUMENTS

| | | | |
|---|---|---|---|
| 2,289,455 | 7/1942 | Ray | 136/232 |
| 3,376,170 | 4/1968 | Logan et al. | 136/233 |
| 3,556,865 | 1/1971 | Levy | 136/233 |
| 3,625,775 | 12/1971 | Mackenzie et al. | 136/233 |
| 3,774,297 | 11/1973 | Wagner | 29/573 |
| 3,893,226 | 7/1975 | Waite | 228/173 A |

FOREIGN PATENT DOCUMENTS 1,811,296  7/1969  Fed. Rep. of Germany ........... 136/233

*Primary Examiner*—Leland A. Sebastian
*Attorney, Agent, or Firm*—Seidel, Gonda & Goldhammer

[57] ABSTRACT

A thermocouple assembly is provided wherein dissimilar metals are joined at a hot junction within a protective annular shield transparent to radiation. The hot junction is formed in situ so as to be in intimate contact with the ID of said shield. When the assembly is mounted on a phase change cup, one of the dissimilar metals is insulated from the cup.

3 Claims, 3 Drawing Figures

METHOD OF MAKING THERMOCOUPLE

RELATED CASE

This application is a division of my copending application Ser. No. 672,100 filed Mar. 31, 1976 now U.S. Pat. No. 4,056,407, and entitled Thermocouple.

BACKGROUND

In the metal industry, it has been common for a period of time to use disposable thermocouples for measuring the temperature of a molten bath and to use disposable thermocouples as part of a phase change device. Such phase change devices are utilized, for example, when detecting the thermal arrest temperature of a molten metal.

Examples of prior art related to disposable thermocouples for use in connection with measuring the temperature of a molten bath include U.S. Pat. Nos. 3,011,005; 3,048,642; 3,493,439; and 3,531,331. Examples of prior art disclosing phase change cups which include a thermocouple are 3,267,732, 3,611,808 and 3,946,594.

Difficulties have been noted, especially in connection with phase change cups, with respect to the appreciable length of time during which the thermocouple hot junction is subjected to considerable stresses. It is often noted that temperature measurements are not perfectly reproducible from one device to the next. It is believed that the discrepancy is due mainly to the manner of forming the thermocouple hot junction on the one hand, and due to the influence of carbonization of resins in the refractory cup which becomes slightly electrically conductive. The present invention overcomes each of these objectionable features.

The thermocouple assembly of the present invention includes dissimilar metals joined at a hot junction within a protective annular shield which is transparent to radiation. The hot junction is formed in situ so as to be in intimate contact with substantially 360° of the inner circumference of said shield. When the thermocouple assembly is applied to a cup of the phase change type, one of the dissimilar metals is electrically insulated from contact with the refractory material from which the cup is made.

Heretofore, it has been conventional to form a hot junction between dissimilar metals for use as a disposable thermocouple by welding and/or twisting together adjacent ends of the dissimilar metal wires. Thereafter, the metal wires are inserted into a straight or U-shaped protective shield from a material such as quartz in a manner so that one end of each of the metal wires projects from the opposite ends of the shield. When the shield is U-shaped, the hot junction is positioned adjacent to the bight of the shield. The thermocouple assembly of the present invention is distinguished from such conventional procedure particularly by forming the hot junction of the juxtaposed ends of the thermocouple wires in situ within the protective shield.

It is an object of the present invention to provide a method of thermocouple assembly which produces more uniform results.

It is another object of the present invention to provide a method of constructing a phase change device which produces more uniform results.

Other objects will appear hereinafter.

For the purpose of illustrating the invention, there is shown in the drawings a form which is presently preferred; it being understood, however, that this invention is not limited to the precise arrangements and instrumentalities shown.

Referring to the drawing in detail, wherein like numerals indicate like elements, there is shown in FIG. 1 a phase change device designated generally as 10.

Figure 1:
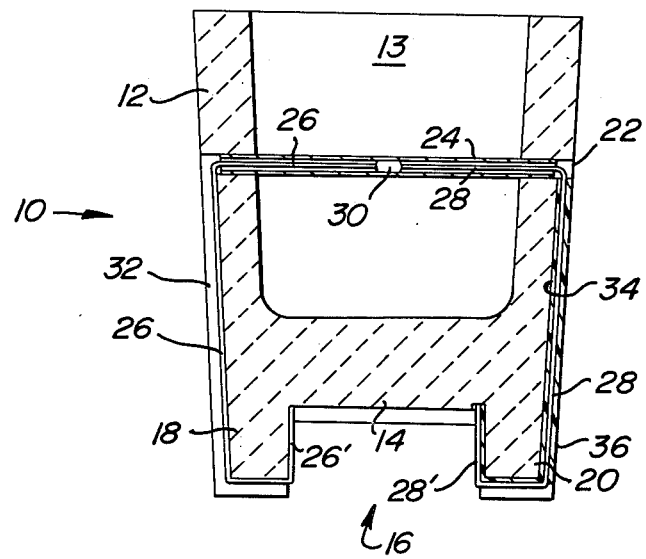
FIG. 1 is a sectional view through a phase change cup.

The phase change device 10 includes a cup 12 made from a refractory material such as that disclosed in the above mentioned patents. The cup 12 has a cavity 13 for receiving a sample of molten metal. The bottom wall 14 of the cup 12 is provided with a recess 16 thereby defining like portions 18 and 20.

A bore 22 extends through oppositely disposed walls of the cup 12. Bore 22 is provided in a location so that its axis will pass through the central axis of cavity 13. A protective shield 24 extends across the cavity 13 and its ends are supported by the bores 22 in the walls of the cup 12. Shield 24 is annular in cross section and transparent to radiation. The preferred material for shield 24 is quartz. Other conventional materials of a similar nature may be utilized.

Figure 2:
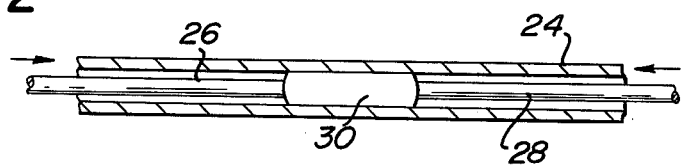
FIG. 2 is an enlarged sectional view at the hot junction of the thermocouple.

The thermocouple wires 26 and 28 may be anyone of the typical thermocouple materials utilized heretofore in connection with disposable thermocouples such as chromel and alumel. The juxtaposed ends of the thermocouple wires 26 and 28 are joined together at the hot junction 30 positioned adjacent to the central axis of cavity 13. The hot junction 30 is formed in situ whereby the wires 26 and 28 are inserted into the shield 24 until they are in abutting contact. Slight pressure is maintained in the direction of the arrow shown in FIG. 2 so as to maintain the thermocouple wires in intimate contact while sufficient heat is applied radially inwardly through the shield 24 to effect a welded hot junction 30, which contacts substantially 360° of the inner circumference of the shield 24.

The thusly formed thermocouple assembly is then inserted through the aligned bores. The exposed portions of the thermocouple wires 26 and 28 are bent downwardly so as to extend into the vertically disposed grooves 32 and 34 on opposite sides of the cup 12. One of the thermocouple wires, such as wire 28 is provided with an electrical insulating sleeve 36 so as to prevent contact between the thermocouple wire 28 and the material of the body of cup 12. The free end portion of thermocouple wire 26 is bent into the recess 16 to thereby form a contact member for coupling with any mating contacts associated with a recorder. Similarly, the free end portion of thermocouple wire 28 is bent into the recess 16 to form a contact portion 28' which is exposed for contact with elements associated with a recorder.

The dimensions of the shield 24 and the thermocouple wires may vary widely. In a typical embodiment of the invention, shield 24 has an OD of 0.069-0.079 inches, and a ID of 0.029-0.039 inches. In connection with such a shield 24, the OD of wires 26 and 28 is 0.025 inches.

The particular embodiment of the cup 12 described above is for illustrative purposes only. Thus, the thermocouple assembly may be utilized in any one of a wide variety of different commercially available cups used as phase change detectors and/or a wide variety of different devices for measuring the temperature of molten baths.

Figure 3:
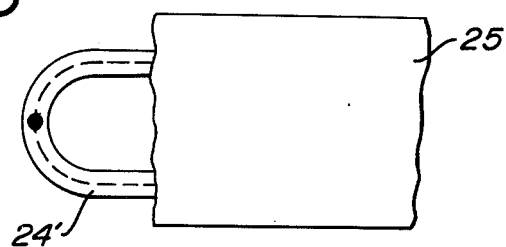
FIG. 3 shows the thermocouple assembly at the immersion end of a lance for measuring the temperature of a bath of molten metal.

The shield 24 may be bent into a U-shape as shown at 24' in FIG. 3 and supported at the immersion end of an expendable lance 25 for measuring the temperature of a bath of molten metal.

The present invention may be embodied in other specific forms without departing from the spirit or essential attributes thereof and, accordingly, reference should be made to the appended claims, rather than to the foregoing specification as indicating the scope of the invention.

It is claimed:

1. A method of making a thermocouple assembly comprising inserting dissimilar metal thermocouple wires into a tubular shield transparent to radiation, maintaining the juxtaposed ends of the wire in contact within said shield while applying heat through said shield to weld said wire ends in situ to form a hot junction whose diameter is greater than the diameter of the wires and wherein said hot junction is in contact with substantially the entire inner circumference of the shield.

2. A method in accordance with claim 1 including applying pressure in an axial direction to each of the wires to maintain the juxtaposed end of the wires in contact.

3. A method in accordance with claim 1 including using a shield having an inner diameter of 0.029 to 0.039 inches while using wires having an outer diameter of about 0.025 inches.